US009267920B2

(12) United States Patent
Anderson et al.

(10) Patent No.: US 9,267,920 B2
(45) Date of Patent: Feb. 23, 2016

(54) MINIATURE SENSOR STRUCTURES FOR ION MOBILITY SPECTROMETERS

(71) Applicant: Implant Sciences Corporation, Wilmington, MA (US)

(72) Inventors: Andrew G. Anderson, Westford, MA (US); Troy A. Velazquez, Somerville, MA (US); Dmitriy V. Ivashin, Peabody, MA (US); Said Boumsellek, San Diego, CA (US)

(73) Assignee: Implant Sciences Corporation, Wilmington, MA (US)

( * ) Notice: Subject to any disclaimer, the term of this patent is extended or adjusted under 35 U.S.C. 154(b) by 0 days.

(21) Appl. No.: 14/190,785

(22) Filed: Feb. 26, 2014

(65) Prior Publication Data

US 2014/0239174 A1     Aug. 28, 2014

Related U.S. Application Data

(60) Provisional application No. 61/769,320, filed on Feb. 26, 2013.

(51) Int. Cl.
    *H01J 49/00*           (2006.01)
    *G01N 27/62*           (2006.01)

(52) U.S. Cl.
    CPC .......... *G01N 27/622* (2013.01); *H01J 49/0013* (2013.01); *H01J 49/00* (2013.01)

(58) Field of Classification Search
    CPC ..... G01N 27/622; H01J 49/0013; H01J 49/00
    USPC ........................................................ 250/288
    See application file for complete search history.

(56) References Cited

U.S. PATENT DOCUMENTS

| | | | |
|---|---|---|---|
| 3,755,891 A | 9/1973 | Muckelroy et al. | |
| 4,475,967 A | 10/1984 | Kanai et al. | |
| 5,021,654 A | 6/1991 | Campbell et al. | |
| 5,028,473 A | 7/1991 | Vitriol et al. | |
| 6,369,383 B1 * | 4/2002 | Cornish ................... | G21K 1/06 250/286 |
| 6,527,890 B1 | 3/2003 | Briscoe et al. | |
| 7,155,812 B1 * | 1/2007 | Peterson ................. | H01C 3/06 250/286 |
| 7,224,258 B2 | 5/2007 | Barge et al. | |
| 7,547,880 B2 | 6/2009 | Landgraf et al. | |
| 7,619,214 B2 | 11/2009 | Miller et al. | |
| 7,736,592 B2 | 6/2010 | Grande et al. | |

(Continued)

FOREIGN PATENT DOCUMENTS

WO     WO 2007/056488 A1     5/2007

OTHER PUBLICATIONS

Liang-Yu Chen, et al, "Packaging Technologies for High Temperature Electronics and Sensors," Ohio Aerospace Institute/NASA Glenn Research Center, Proceedings of MFPT 2013/ISA's 29th IIS, 6 pps.

*Primary Examiner* — Wyatt Stoffa
(74) *Attorney, Agent, or Firm* — Muirhead and Saturnelli, LLC

(57) ABSTRACT

For ion mobility spectrometry applications, a desired shape of a sensor structure may be created by forming a desired shape from a ceramic material, such as aluminum nitride. In various embodiments, the sensor structure may be formed using discrete individual ceramic sheets and/or from a preformed ceramic tube. Via holes are formed into the sensor structure to provide for efficient circuitry configurations of the IMS drift tube and/or providing electrical connections between the interior and exterior of the drift tube.

15 Claims, 7 Drawing Sheets

(56) References Cited

U.S. PATENT DOCUMENTS

| | | | |
|---|---|---|---|
| 8,173,959 B1 | 5/2012 | Boumsellek et al. | |
| 8,314,383 B2 | 11/2012 | Wu | |
| 8,479,585 B2 | 7/2013 | Shaw-Klein | |
| 8,716,655 B2* | 5/2014 | Chou | H01J 49/0013 250/281 |
| 2002/0074496 A1* | 6/2002 | Sadayama | H01J 37/3056 250/311 |
| 2006/0076482 A1* | 4/2006 | Hobbs | H01J 49/009 250/287 |
| 2007/0272852 A1* | 11/2007 | Miller | G01N 27/624 250/288 |
| 2008/0185512 A1* | 8/2008 | Miller | H01J 49/004 250/287 |
| 2009/0189064 A1* | 7/2009 | Miller | G01N 30/7206 250/282 |
| 2010/0224695 A1 | 9/2010 | Wu et al. | |
| 2011/0001044 A1* | 1/2011 | Chou | H01J 49/0013 250/282 |
| 2011/0210244 A1* | 9/2011 | Wu | H01J 49/004 250/283 |
| 2012/0273669 A1 | 11/2012 | Ivashin et al. | |
| 2012/0326020 A1* | 12/2012 | Ivashin | G01N 27/624 250/282 |
| 2013/0009053 A1* | 1/2013 | Wu | H01J 49/004 250/282 |
| 2013/0264475 A1* | 10/2013 | Ivashin | H01J 49/105 250/290 |

\* cited by examiner

MINIATURE SENSOR STRUCTURES FOR ION MOBILITY SPECTROMETERS

RELATED APPLICATIONS

This application claims priority to U.S. Provisional App. No. 61/769,320, filed Feb. 26, 2013, entitled "Making Miniature Drift Tubes for Ion Mobility Spectrometers," which is incorporated herein by reference.

TECHNICAL FIELD

This application is related to the field of chemical analysis and, in particular, ion mobility spectrometry.

BACKGROUND OF THE INVENTION

Ion mobility spectrometry (IMS) utilizes relative low electric fields to propel ions through a drift gas chamber and separate these ions according to their drift velocity. In IMS, the ion drift velocity is proportional to the field strength and thus an ion's mobility (K) is independent of the applied field. In the IMS both analyte and background molecules are typically ionized using radioactive alpha or beta emitters and the ions are injected into a drift tube with a constant low electric field (300 V/cm or less) where they are separated on the basis of their drift velocity and hence their mobility. The mobility is governed by the ion collisions with the drift gas molecules flowing in the opposite direction. The ion-molecule collision cross section depends on the size, the shape, the charge, and the mass of the ion relative to the mass of the drift gas molecule. The resulting chromatogram is compared to a library of known patterns to identify the substance collected. Since the collision cross section depends on more than one ion characteristic, peak identification is not unique. IMS systems measure a secondary and less specific property of the target molecule—the time it takes for the ionized molecule to drift through a tube filled with a viscous gas under an electric field—and the identity of the molecule is inferred from the intensity vs time spectrum.

Other mobility-based separation techniques include high-field asymmetric waveform ion mobility spectrometry (FAIMS) also known as Differential Mobility Spectrometry (DMS). FAIMS or DMS is a detection technology which can operate at atmospheric pressure to separate and detect ions. Compared to conventional ion mobility, FAIMS/DMS devices operate at much higher fields (~10,000 V/cm) where ion mobilities become dependent on the applied field. FAIMS/DMS devices may operate in conjunction with IMS drift tube devices in spectrometers having multiple stages. For specific descriptions of features and uses of instruments for ion detection and chemical analysis, including features of IMS drift tube devices used in connection with one or more FAIMS/DMS devices, among other components, reference is made to U.S. Pat. No. 8,173,959 B1 to Boumsellek et al., entitled "Real-Time Trace Detection by High Field and Low Field Ion Mobility and Mass Spectrometry," U.S. Pub. No. 2012/0273669 A1 to Ivashin et al., entitled "Chemical Analysis Using Hyphenated Low and High Field Ion Mobility," and U.S. Pub. No. 2012/0326020 A1 to Ivashin et al., entitled "Ion Mobility Spectrometer Device with Embedded FAIMS," which are all incorporated herein by reference.

Known IMS device construction techniques include the use of alternate stacking of metallic and insulator rings to produce sensor structures. These sensors structures, such as IMS drift tubes, are used in the ion transport and analysis applications at atmospheric or near atmospheric pressure. Further, other techniques are known for producing IMS sensor structures using ceramic material rolling processes. For example, U.S. Pat. No. 7,155,812 B1 to Peterson et al., entitled "Method for Producing a Tube," and which is incorporated herein by reference, discloses a process of rolling a pliable green (i.e. prefired) ceramic sheet around a form for multiple revolutions and in which electrical conductors are disposed on a surface of the ceramic sheet. The rolled ceramic sheet is subject to pressure and fired to produce the IMS drift tube. The ceramic may be a low temperature co-fired ceramic (LTCC). It is noted that in some cases use of a continuously rolled sheet process may limit the functionality and complexity of circuit or sensor components of the IMS drift tube. Other techniques for producing three-dimensional ceramic circuit structures are described in U.S. Pat. No. 6,527,890 to Briscoe et al., U.S. Pat. No. 5,028,473 to Vitriol et al., U.S. Pat. No. 4,475,967 to Kanai et al., and U.S. Pat. No. 3,755,891 to Muckelroy et al., all of which are incorporated herein by reference.

Accordingly, it would be desirable to provide advantageous and efficient techniques for producing high performance, low cost, miniature drift tubes or other sensor structures for IMS devices on a large production scale.

SUMMARY OF THE INVENTION

According to the system described herein, a method for making a sensor structure includes forming a shaped structure made of a high temperature, non-electrically-conductive ceramic material. At least one via hole is formed in the shaped structure. Circuitry features are formed on the shaped structure. The shaped structure is processed to obtain a sensor structure. The ceramic material may be aluminum nitride or alumina, and the sensor structure may be an ion mobility spectrometry drift tube. Forming the shaped structure may include applying and forming at least two discrete sheets of the high temperature, non-electrically-conductive ceramic material into a structure having a desired shape, and the at least one via hole in the shaped structure may be formed to provide a via hole that connects the interior and exterior of the shaped structure. Forming the shaped structure may include preforming a solid tube of the high temperature, non-electrically-conductive ceramic material, and the at least one via hole may be machined into the solid tube. Forming the circuitry features may include forming conductive or resistive features on the shaped structure using an ink deposition process.

According further to the system described herein, a sensor structure includes a shaped structure made of a high temperature, non-electrically-conductive ceramic material. Circuitry features are formed on the shaped structure. At least one via hole is formed in the shaped structure. The ceramic material may be aluminum nitride or alumina, and the sensor structure may be an ion mobility spectrometry drift tube. The shaped structure may be formed from applying and forming at least two discrete sheets of the high temperature, non-electrically-conductive ceramic material into a structure having a desired shape, and the at least one via hole in the shaped structure may be formed to provide a via hole that connects the interior and exterior of the shaped structure. The shaped structure may include a preformed solid tube of the high temperature, non-electrically-conductive ceramic material, and the at least one via hole may be machined into the solid tube. The circuitry features may include be formed by forming conductive or resistive features on the shaped structure using an ink deposition process.

According further to the system described herein, an ion mobility spectrometer device includes an ion source, an analyzer component, and a drift tube coupled between the ion source and the analyzer component. The drift tube includes a shaped structure made of a high temperature, non-electrically-conductive ceramic material. Circuitry features are formed on the shaped structure. At least one via hole is formed in the shaped structure. The ceramic material may be aluminum nitride or alumina, and the sensor structure may be an ion mobility spectrometry drift tube. The shaped structure may be formed from applying and forming at least two discrete sheets of the high temperature, non-electrically-conductive ceramic material into a structure having a desired shape, and the at least one via hole in the shaped structure may be formed to provide a via hole that connects the interior and exterior of the shaped structure. The shaped structure may include a preformed solid tube of the high temperature, non-electrically-conductive ceramic material, and the at least one via hole may be machined into the solid tube. The circuitry features may include be formed by deposited conductive or resistive features that are deposited on the shaped structure using an ink deposition process.

BRIEF DESCRIPTION OF THE DRAWINGS

Embodiments of the system described herein are explained with reference to the several figures of the drawings, which are briefly described as follows.

DETAILED DESCRIPTION OF VARIOUS EMBODIMENTS

Figure 1:
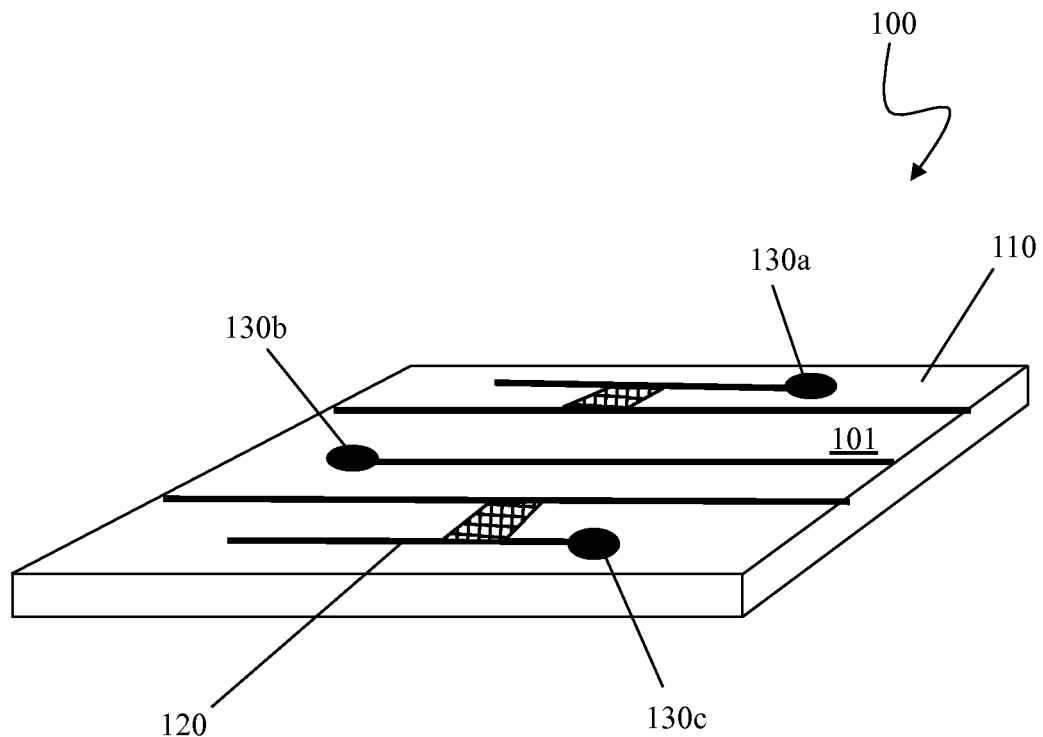
FIG. 1 is a schematic illustration showing an individual ceramic sheet that may be used in connection with making high performance, low cost, miniature sensors structures on a large production scale using ceramic materials according to the embodiment of the system described herein.

FIG. 1 is a schematic illustration 100 showing an individual ceramic sheet 101 that may be used in connection with making high performance, low cost, miniature sensors structures on a large production scale using ceramic materials according to the embodiment of the system described herein. The sensor structure may be created in part or in whole from multiple discrete individual sheets, like the sheet 101, that may be flat pliable sheets of green-state ceramic material 110. In various embodiments, the sensor structure may, for example, be an ion guide and/or an IMS drift tube, as further discussed elsewhere herein.

In an embodiment, the ceramic material 110 may be aluminum nitride, alumina and/or other high temperature non-electrically conductive material. In particular, aluminum nitride has an advantageously high thermal conductivity, for example up to one hundred times greater than the thermal conductivity of low temperature co-fired ceramic (LTCC), and thereby may be beneficially used in IMS drift tubes or other sensor structures since the use of aluminum nitride allows IMS device products to come up to temperature faster. Further use of aluminum nitride mitigates and/or eliminates cold spots which, if present, lead to extended clear down times after the introduction of a sample into the drift tube.

A desired shape of each sensor structure may be created by applying, forming and joining the individual sheets into the desired shape, for example, by applying the sheets as layers around either a male or female form tool such as a cylindrical mandrel or other shape, as further discussed elsewhere herein. During the green state of the sheet(s) 101, conductive features 120, such as discrete or continuous metal surfaces, may be placed on the individual ceramic sheet 101 by screen printing or other deposition methods. The features 120 may serve as electrodes establishing electrostatic fields to control ion motion, current-based heaters, electronic shields, bonding surfaces for secondary attachment, and/or other appropriate circuitry structure or other sensor features. In various embodiments, the layers may have the features 120 on one surface of the sheet 101, both surfaces and/or neither surface as needed or desirable to create a required circuit structure. One or more via holes 130a, 130b, 130c may also be formed into the sheet 101, as further discussed elsewhere herein.

Figure 2:
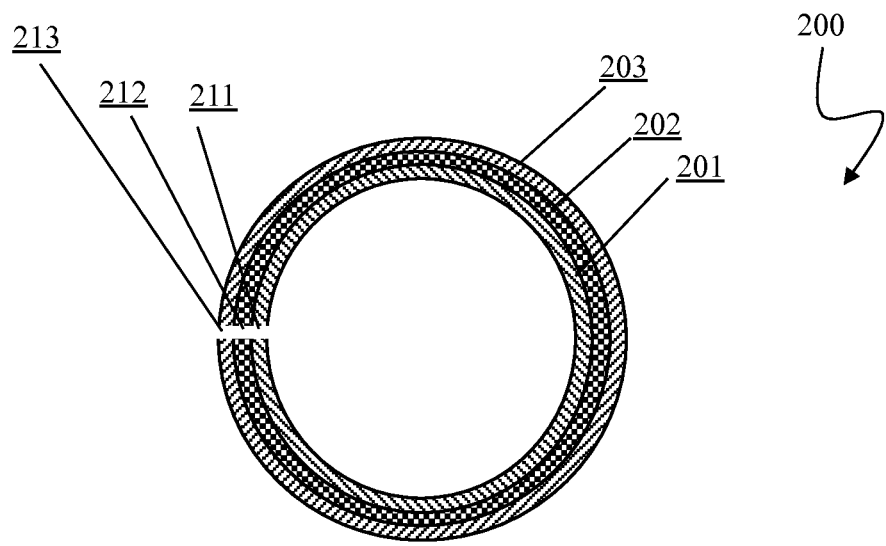
FIG. 2 is a schematic illustration showing an end view of multiple ceramic sheets that have been layered over one another around a shape, such as a cylindrical mandrel in connection with producing an IMS sensor structure, such as an IMS drift tube.

FIG. 2 is a schematic illustration 200 showing an end view of multiple ceramic sheets 201, 202, 203 that have been layered over one another around a shape, such as a cylindrical mandrel in connection with producing an IMS sensor structure, such as an IMS drift tube. Each of the ceramic sheets 201, 202, 203 may be like the described ceramic sheet of FIG. 1 but having particular conductive and circuitry features as required to create the desired circuitry configuration of the IMS drift tube. Although three sheets 201-203 are illustrated, any appropriate number of sheets may be used for a desired structure. According to the system described herein, the design and layering of the ceramic sheets 201, 202, 203 may be such that each sheet, when formed into the desired shape, is positioned according to desired circuitry configurations. For example, the ceramic sheets 201, 202, 203 may be designed, when layered, to be applied such that abutting ends of the ends positioned along a single seam for desired circuitry configurations. The sheets 201, 202, 203 may each contain one or more via holes 211, 212, 213. The via holes 211, 212, 213 may be provided at locations that facilitate subsequent electrical connections among the layers 201, 202, 203 to form the desired circuit structure. For example, in the illustrated embodiment shown in FIG. 2, the via holes 211, 212, 213 provided in each of the sheets may form one or more via holes through from the inside of the drift region of the IMS drift tube to the outside of the IMS device. Each of the ceramic sheets 201, 202, 203 may be made of aluminum nitride, alumina and/or other high temperature non-electrically conductive material. The via holes 211, 212, 213 may be metallized, as further discussed herein, and may include use of contact pads to enable electrical connections between circuitry features of the sheets 201, 202, 203 according to various embodiments of the system described herein. The structure may be subject to a high pressure and temperature environment to produce a fused monolithic sensor structure, such as an IMS drift tube.

Figure 3:
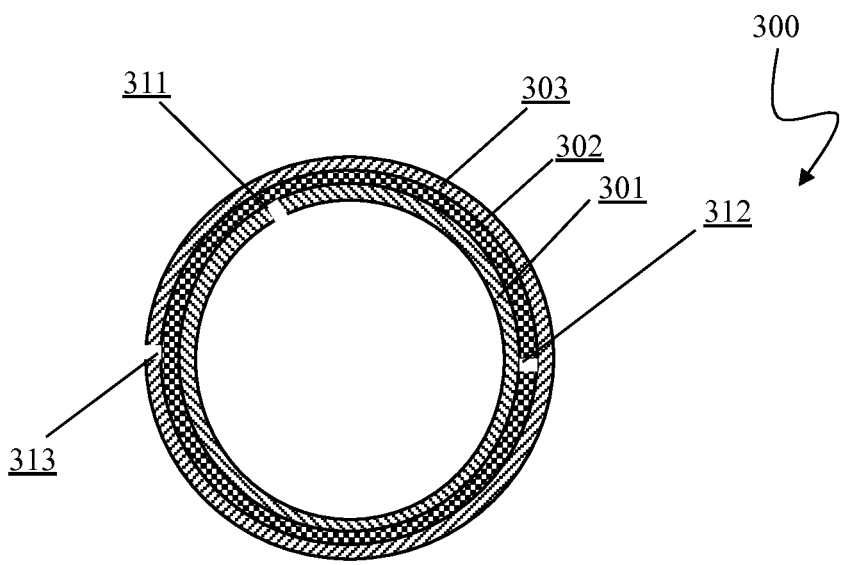
FIG. 3 is a schematic illustration showing an end view for another embodiment, as compared to FIG. 2, in which multiple ceramic sheets have been layered over one another around a shape, such as a cylindrical mandrel in connection with producing an IMS sensor structure, such as an IMS drift tube.

FIG. 3 is a schematic illustration 300 showing an end view for another embodiment, as compared to FIG. 2, in which multiple ceramic sheets 301, 302, 303 have been layered over one another around a shape, such as a cylindrical mandrel in connection with producing an IMS sensor structure, such as an IMS drift tube. In the illustrated embodiment, the via holes 311, 312, 313 formed are staggered throughout the width of the IMS drift tube. The staggering of the via holes 311, 312, 313 may be to provide the suitable circuitry configuration of the IMS drift tube. Each of the ceramic sheets 301, 302, 303 may be made of aluminum nitride, alumina and/or other high temperature non-electrically conductive material. It is further noted that the sheets 301, 302, 303 themselves, may be layered such that abutting ends of the sheets, after application of the sheets, are staggered around the circumference of the drift tube in accordance with designed circuitry configurations of circuitry features on the sheets 301, 302, 303 that may be electrically connected using the via holes 311, 312, 313. It is also noted that various combinations of the embodiments described in connection with FIGS. 2 and 3 may be appropriately used according to the system described herein.

Figure 4A:
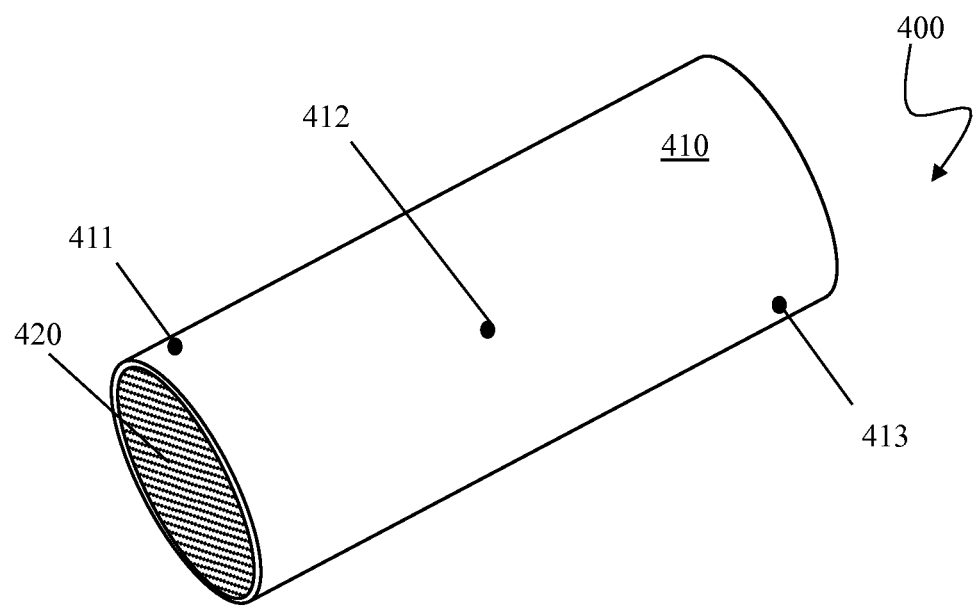
FIGS. 4A and 4B are schematic illustrations showing an alternative construction for an IMS drift tube according to an embodiment of the system described herein.
Figure 4B:
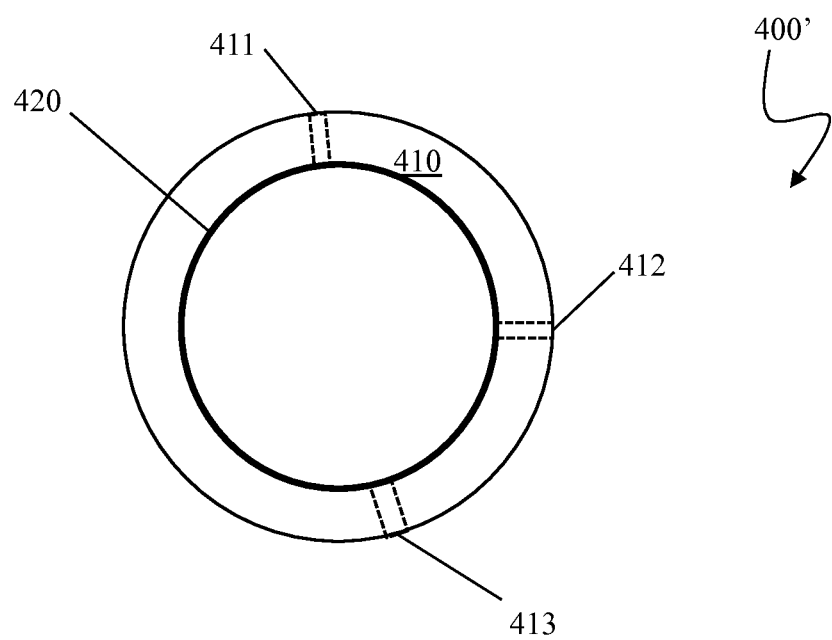

FIGS. 4A and 4B are schematic illustrations 400, 400' showing an alternative construction for an IMS drift tube according to an embodiment of the system described herein. FIG. 4A is a schematic illustration of a solid tube 410 that, in the alternative construction technique, may be pre-formed from a high temperature non-electrically conductive material, such as alumina or, in particular, aluminum nitride. FIG. 4B is schematic illustration of an end view of the solid tube 410. One or more via holes 411, 412, 413 may be drilled or otherwise machined through the sheet 101 at predetermined locations to facilitate subsequent electrical connections from the inside of the drift region of the tube 410 to the outside. The inside drift region may be metallized with a layer 420, such as by a metallic ink deposition process, to support the creation of electrode rings of the tube 410. In an embodiment, the metallization may be through the use of thick film metallization, and the via holes 411-413, with associated connection pads, may also be metallized so as to electrically connect from the metallized surface of the interior drift region to the exterior of the IMS device. It should also be noted that, in addition to the via holes 411-413, electrical connections may be accomplished by adding traces along the surfaces and edges of the ceramic material. As further described elsewhere herein, the exterior of the device may also be metallized to form electrical traces, shielding, or heater circuits and/or other features in accordance with the discussion herein. The metallization may be accomplished using different metals so as to mate the needs of the surface with the application. For example, the metal on the drift region may be selected for low chemical reactivity while the metal in the via and associated pads may be selected to support secondary operations such as filling, brazing or soldering.

Because the metallization process may be imprecise, secondary machining may be provided, where necessary, for configuration of the sensor structure in order to remove any undesired metallization and restore electrical isolation between metallized regions inside and outside of the device. In an IMS configuration, the remaining metallization inside the drift region may take the form of separated concentric rings each connected by one or more of the metallized via holes. Hermetic sealing of the via holes may be accomplished by any number of standard methods including but not limited to soldering, brazing of filler preforms, glass sealing, adhesives etc. The tube 410 may be enclosed by attaching drift region cap structures of an IMS device, as further discussed elsewhere herein. The cap structures may be attached mechanically to facilitate disassembly or more permanently by soldering, brazing of preforms, glass sealing, adhesives etc.

Additionally and/or alternatively, in other embodiments, more precise methods of metallic ink deposition may be used that may avoid the need for secondary machining noted above. For example, technology is known that enables use of computer numerical control (CNC) controlled ink deposition tips that allow the depositing either resistive and/or conductive inks onto either the inside or outside of a curved surface. Reference is made to techniques and products of Ohmcraft, a division of Micropen Technologies Corporation. Such products and techniques may be used to produce resistive and conductive elements on the interior and exterior of a drift tube made of alumina, aluminum nitride or other high temp electrically insulating material, according to an embodiment of the system described herein. Reference is made, for example, to U.S. Pat. No. 7,224,258 B2 to Barge et al., entitled "Fine Line Thick Film Resistors by Photolithography," U.S. Pat. No. 7,736,592 B2 to Grande et al., entitled "Microfluidic Devices Fabricated by Direct Thick Film Writing and Methods thereof," and U.S. Pat. No. 8,479,585 B2 to Shaw-Klein, entitled "Full-Text Pressure Sensing or Force Generating Device," which are all incorporated herein by reference.

Figure 5:
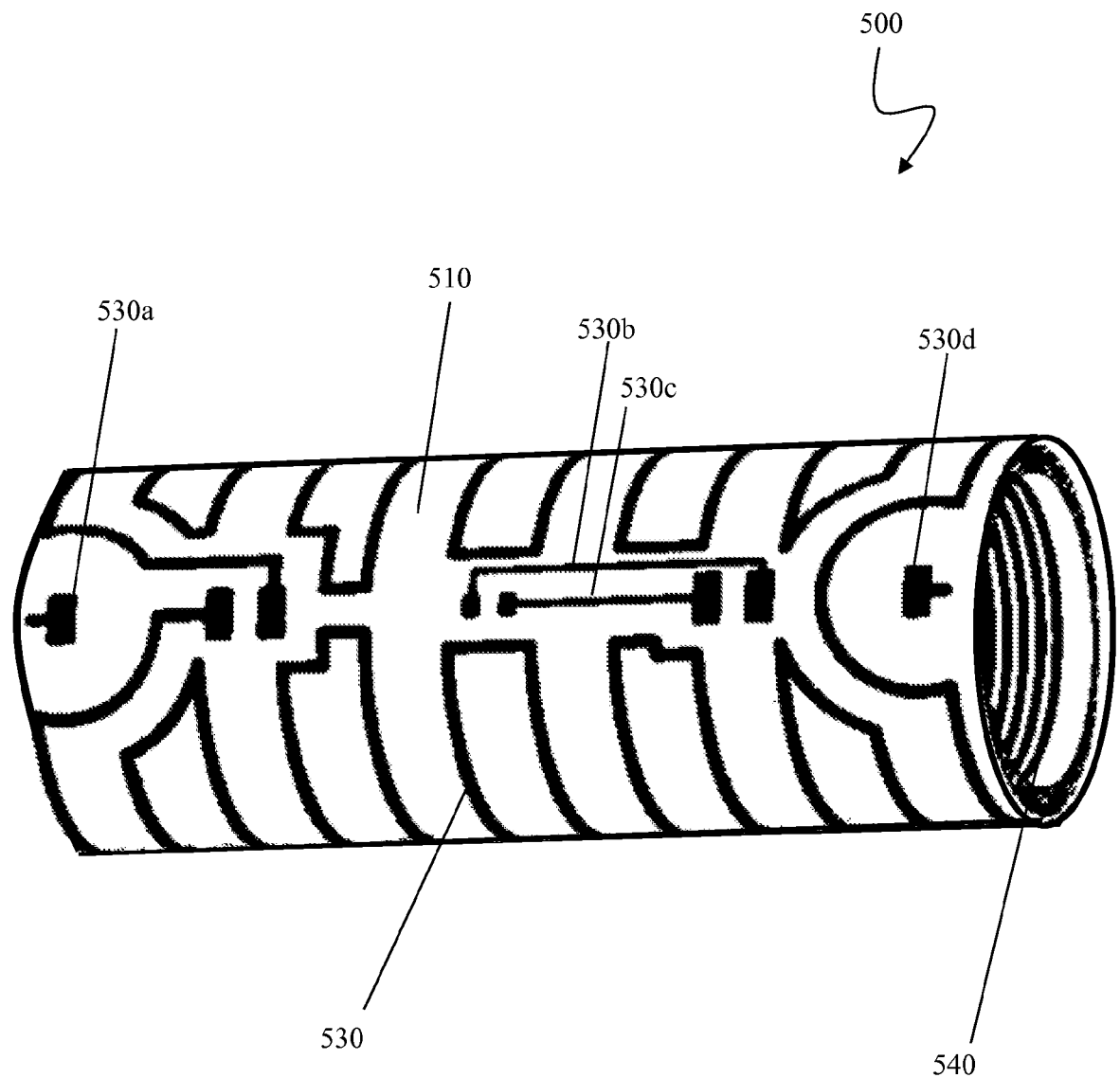
FIG. 5 is a schematic illustration showing an IMS drift tube produced according to an embodiment of the system described herein.

FIG. 5 is a schematic illustration showing an IMS drift tube 500 produced according to an embodiment of the system described herein. The tube shape of the drift tube 500 may be formed by a high temperature electrically-insulating ceramic material 510, such aluminum nitride and/or alumina. Electrical components and structure 520 may be formed on the outer surface of the drift tube 500, such as a resistive heater trace. Conductive traces 530a-d leading from pads and via holes to connection points may also be formed. Inside components 540 may be formed and provided for the drift region of the tube 500. For example, in various embodiments, the inside components 540 may be electrode rings formed from a deposition method and/or may, for example, be a continuous spiral of resistive ink that may be used to replace discrete electrodes and an external resistor network.

Figure 6:
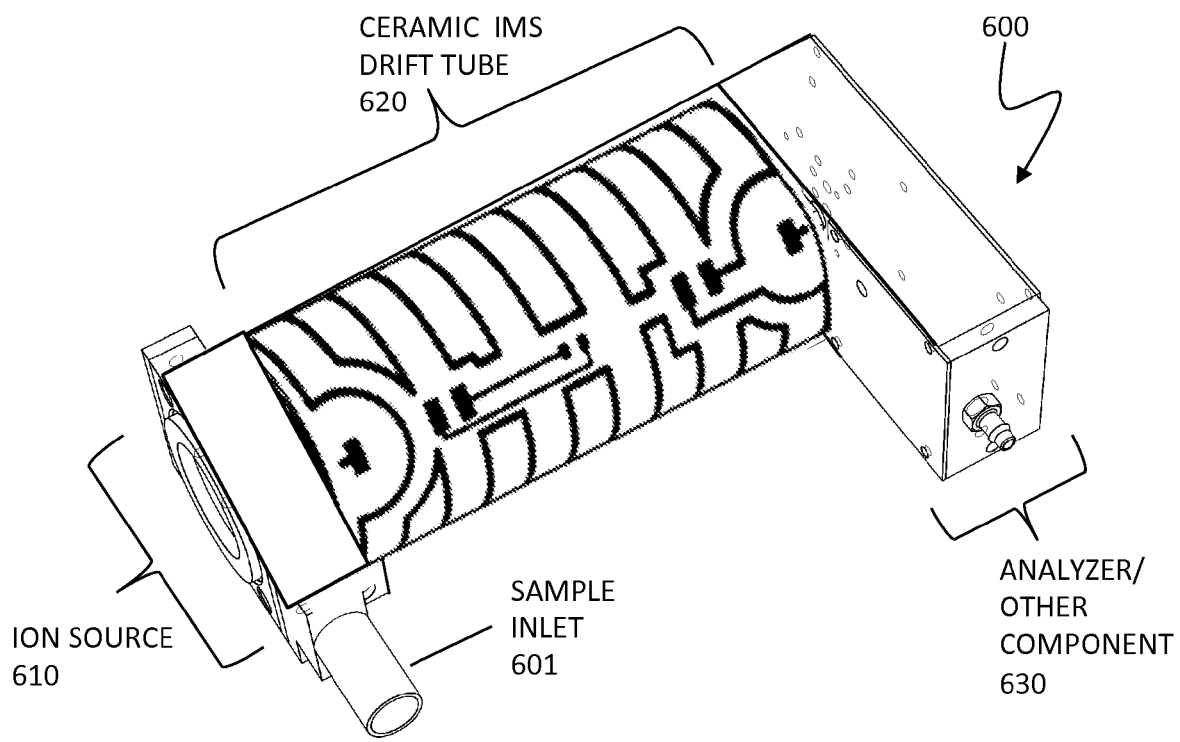
FIG. 6 is schematic perspective illustration showing an example IMS device produced according to an embodiment of the system described herein.

FIG. 6 is schematic perspective illustration showing an example IMS device 600 produced according to an embodiment of the system described herein. The device 600 may include an ionizer/ion source 610, a ceramic IMS drift tube 620, and an analyzer component 630, such as a detector and/or other component such one or more additional analytical component, for example a FAIMS/DMS component, as appropriate or desirable for the IMS analysis being performed. The ionizer/ion source 610 may provide a continuous or a pulsed ion current depending on an operational mode. In an embodiment, the ionizer/ion source 610 may include a pulsed ion source, such as a spark ion source, that may send either individual packets of ions or a continuous flow of ions by varying the frequency. Additionally or alternatively, a continuous ion source may be used including a DC corona or a radioactive source via an ion gate placed at the entrance of the IMS drift tube 620. The IMS drift tube 620 may be formed by using ceramic material, as according to the embodiments discussed elsewhere herein, that may include circuitry and electrical features necessary to form the drift tube 620.

The system described herein offers multiple advantages in the production of sensor structures (e.g. drift tubes) for IMS devices. In particular, manufacturing costs are significantly reduced by a reduction in discrete components. Construction may include use of inert materials capable of high temperature operation. The use of ceramic materials, such as aluminum nitride, provides thermal conductivity of aluminum while maintaining electrical isolation, and which supports fast and even heating. Higher density of electrodes is provided using small width traces required for miniature drift tubes. Superior inherent hermeticity is provided by a reduction in the number of sealing joints and overall sealing length. The concept is scalable to support different sized drift regions. Metallization enables multiple functional and connectivity elements in a single part.

The method and choice of materials according to the system described herein further provides performance advantages. In particular, improved system reliability is provided through simplified and flexible designs. Improved resolving power is provided through the use of high density electrodes. Extended range of detectable chemical compounds is provided through rapid thermal cycling. There is a lack of contamination and better moisture control through the use of hermetic tubes. Rapid thermal cycling over a wide range of temperature settings is enabled by the use of intimate heater elements. Reduced chemical noise is provided by the elimination of polymeric materials frequently required in conventional sensor construction.

Figure 7:
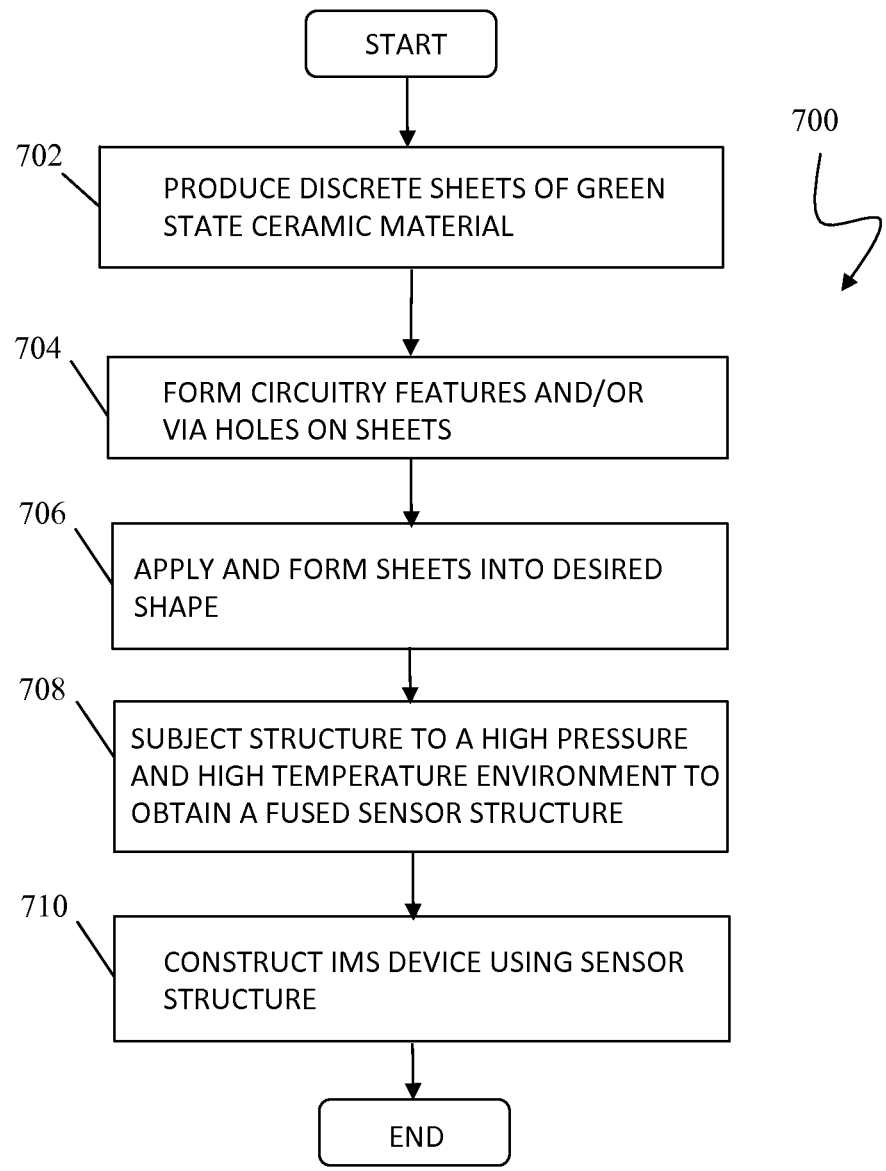
FIG. 7 is a flow diagram showing processing for making a sensor structure according to an embodiment of the system described herein.

FIG. 7 is a flow diagram 700 showing processing for making a sensor structure according to an embodiment of the system described herein. At a step 702, one or more discrete sheets of green-state ceramic material are produced. In various embodiments, the ceramic material may be aluminum nitride, alumina and/or other high temperature, non-electrically-conductive ceramic material. The discrete ceramic sheets may be flexibly manufactured and sized for a desired application and configuration of an IMS device. After the step 702, at a step 704, circuitry features are formed into the discrete ceramic sheets for the desired IMS sensor structure, and including the formation of via holes in the sheets at desired locations. As further discussed elsewhere herein, the circuitry features may be applied by screen printing or other deposition methods.

After the step 704, at a step 706, the discrete ceramic sheets with deposited conductive features are formed into a desired shape, such as by applying the sheets around a cylindrical mandrel. In various embodiments, after applying the sheets, the via holes may be staggered through the thickness of the tube so as to enable appropriate circuitry configurations and/or the via holes in the sheets may aligned co-linearly in connection with the sheet layering to produce a via hole through from the interior to the exterior of the tube. After the step 706, at a step 708, the structure is subject to a high pressure and temperature environment to produce a fused monolithic sensor structure, such as an IMS drift tube. After the step 708, at a step 710, the sensor structure may be used in constructing an IMS device, such as by attaching appropriate cap structures to an IMS drift tube suitable for an IMS device and operation thereof. After the step 710, processing is complete.

Figure 8:
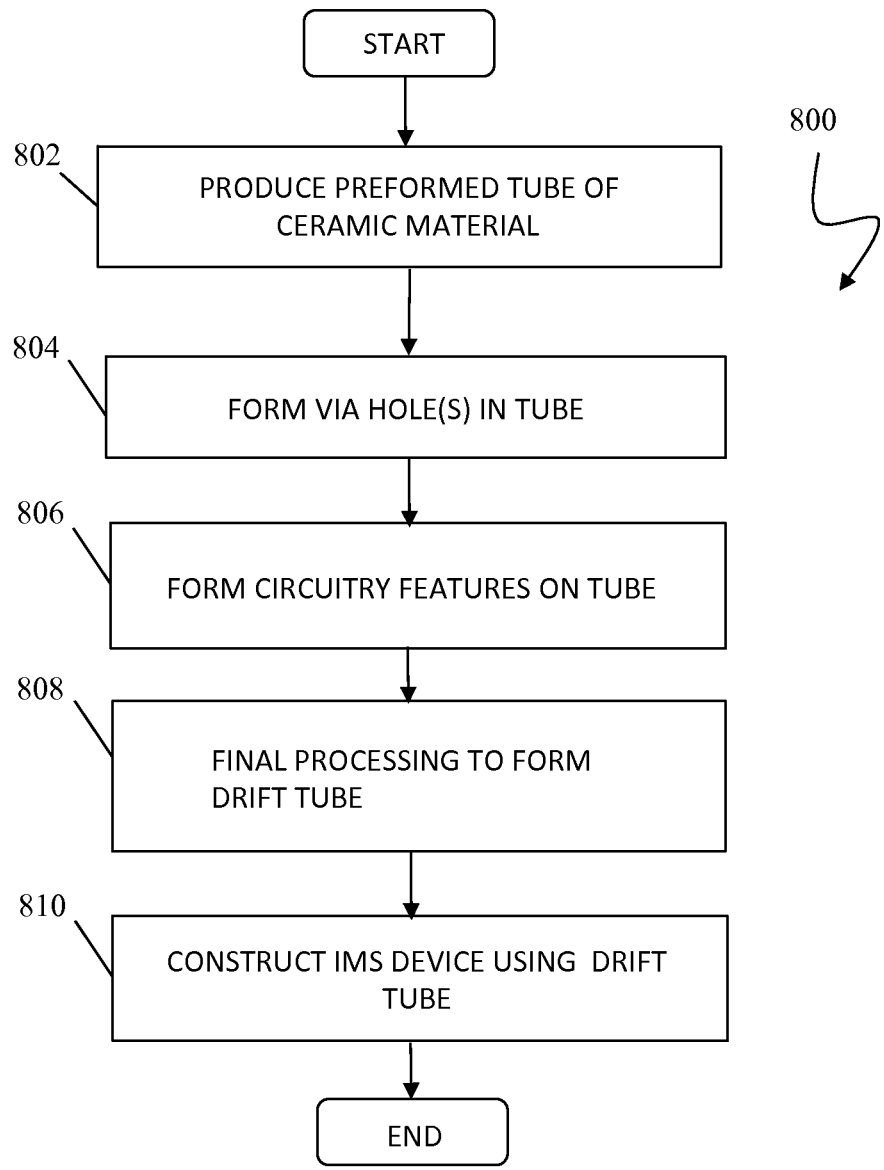
FIG. 8 is a flow diagram showing processing for making a sensor structure according to another embodiment of the system described herein.

FIG. 8 is a flow diagram 800 showing processing for making a sensor structure according to another embodiment of the system described herein. At a step 802, a preformed shape, such as a tube, of ceramic material is produced. In various embodiments, the ceramic material may be aluminum nitride, alumina and/or other high temperature, non-electrically-conductive ceramic material. After the step 802, at a step 804, at least one via hole is formed into the ceramic tube from the structure. The at least one via hole is formed from the exterior to the interior of the tube. After the step 804, at a step 806, circuitry features are formed onto the tube. The circuitry features may include features formed on the interior and exterior of the tube. It is noted that the ordering of steps 804 and 806 may be interchanged as appropriate. In an embodiment, the features may be formed by a metallization process. For example, the interior of the tube may be metallized in order to produce electrode rings of the drift region of the tube. A secondary operation may be performed thereafter in order to make the circuitry features more precise and remove undesired metallization and/or restore electrical isolation between metallized regions. In other embodiments, a deposition process may be used that may avoid the need for secondary machining noted above. For example, as discussed elsewhere herein, technology is known that enables use of CNC controlled ink deposition tips that allow the depositing of either resistive and/or conductive inks onto either the inside or outside of a curved surface using an ink deposition process.

After the step 806, at a step 808, the structure may be subject to any additional processing to finalize the circuitry, such as by a firing of deposited inks, where required in order to produce a sensor structure, such as an IMS drift tube. After the step 808, at a step 810, the sensor structure may be used in constructing an IMS device, such as by attaching appropriate cap structures to an IMS drift tube suitable for an IMS device and operation thereof. After the step 810, processing is complete.

Various embodiments discussed herein may be combined with each other in appropriate combinations in connection with the system described herein. Additionally, in some instances, the order of steps in the flowcharts, flow diagrams and/or described flow processing may be modified, where appropriate. Further, various aspects of the system described herein may be implemented using software, hardware, a combination of software and hardware and/or other computer-implemented modules or devices having the described features and performing the described functions. The system may further include a display and/or other computer components for providing a suitable interface with a user and/or other computers.

In connection with applicable control processing, software implementations of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for making a substantially cylindrical sensor structure, comprising:
    forming a substantially cylindrically shaped structure made of a high temperature, non-electrically-conductive ceramic material, by applying at least two discrete sheets of the high temperature, non-electrically-conductive ceramic material as overlaying layers about a cylindrical mandrel to form the shaped structure;

forming at least one via hole in each of the at least two discrete sheets;

forming circuitry features on each of the at least two discrete sheets, wherein the at least one via hole and the circuitry features are formed in each of the at least two discrete sheets before applying the at least two discreet sheets as overlaying layers to form the shaped structure; and processing the shaped structure to obtain the substantially cylindrical sensor structure;

wherein the ceramic material is aluminum nitride or alumina.

2. The method according to claim 1, wherein the sensor structure is an ion mobility spectrometry drift tube.

3. The method according to claim 1, wherein the at least one via hole formed in each of the at least two discrete sheets together are disposed to provide a via hole that connects an interior and an exterior of the shaped structure.

4. The method according to claim 1, wherein forming the circuitry features includes forming conductive or resistive features on the at least two discrete sheets using an ink deposition process.

5. The method according to claim 1, wherein the at least one via hole in each of the at least two discrete overlaying layers is formed to electrically connect the circuitry features of at least one adjacent layer independently of whether a through-via hole is formed from an interior to an exterior of the shaped structure.

6. The method according to claim 1, wherein the shaped structure includes at least three discrete overlaying layers, and wherein the at least one via hole formed in at least one middle layer of the at least three discrete overlaying layers is formed to electrically connect the circuitry features of layers adjacent to the at least one middle layer independently of whether a through-via hole is formed from an interior to an exterior of the shaped structure.

7. A cylindrical sensor structure, comprising:

a substantially cylindrical shaped structure made of a high temperature, non-electrically-conductive ceramic material, having at least two discrete sheets of the high temperature, non-electrically-conductive ceramic material applied as overlaying layers of the shaped structure;

circuitry features formed on each of the at least two discrete sheets of the shaped structure; and at least one via hole formed in each of the at least two discrete sheets of the shaped structure, wherein the at least one via hole in each of the at least two discrete sheets electrically connects the circuitry features of at least one adjacent layer independently of whether a through-via hole is formed from an interior to an exterior of the shaped structure;

wherein the ceramic material is aluminum nitride or alumina.

8. The sensor structure according to claim 7, wherein the sensor structure is an ion mobility spectrometry drift tube.

9. The sensor structure according to claim 7, wherein the at least one via hole formed in each of the at least two discrete sheets together are disposed to provide a via hole that connects an interior and an exterior of the shaped structure.

10. The sensor structure according to claim 7, wherein the circuitry features are formed by deposited conductive or resistive features that are deposited on the at least two discrete sheets using an ink deposition process.

11. The sensor structure according to claim 7, wherein the shaped structure includes at least three discrete overlaying layers, and wherein the at least one via hole formed in at least one middle layer of the at least three discrete overlaying layers is formed to electrically connect the circuitry features of layers adjacent to the at least one middle layer independently of whether a through-via hole is formed from an interior to an exterior of the shaped structure.

12. An ion mobility spectrometer device, comprising:

an ion source;

an analyzer component; and a drift tube coupled between the ion source and the analyzer component, wherein the drift tube includes:

a substantially cylindrical shaped structure made of a high temperature, non-electrically-conductive ceramic material having at least two discrete sheets of the high temperature, non-electrically-conductive ceramic material applied as overlaying layers of the shaped structure;

circuitry features formed on each of the at least two discrete sheets of the shaped structure; and at least one via hole formed in each of the at least two discrete sheets of the shaped structure, wherein the at least one via hole in each of the at least two discrete sheets electrically connects the circuitry features of at least one adjacent layer independently of whether a through-via hole is formed from an interior to an exterior of the shaped structure;

wherein the ceramic material is aluminum nitride or alumina.

13. The ion mobility spectrometer device according to claim 12, wherein the at least one via hole formed in each of the at least two discrete sheets together are disposed to provide a via hole that connects an interior and an exterior of the shaped structure.

14. The ion mobility spectrometer device according to claim 12, wherein the circuitry features are formed by deposited conductive or resistive features that are deposited on the at least two discrete sheets using an ink deposition process.

15. The ion mobility spectrometer device according to claim 12, wherein the shaped structure includes at least three discrete overlaying layers, and wherein the at least one via hole formed in at least one middle layer of the at least three discrete overlaying layers is formed to electrically connect the circuitry features of layers adjacent to the at least one middle layer independently of whether a through-via hole is formed from an interior to an exterior of the shaped structure.

* * * * *